US007544165B2

(12) United States Patent
Mamayek

(10) Patent No.: US 7,544,165 B2
(45) **Date of Patent: *Jun. 9, 2009**

(54) DYNAMICALLY CONFIGURABLE ULTRASOUND TRANSDUCER WITH INTEGRAL BIAS REGULATION AND COMMAND AND CONTROL CIRCUITRY

(75) Inventor: Donald S. Mamayek, Mountain View, CA (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 519 days.

This patent is subject to a terminal disclaimer.

(21) Appl. No.: 10/971,457

(22) Filed: Oct. 21, 2004

(65) Prior Publication Data

US 2005/0054933 A1 Mar. 10, 2005

Related U.S. Application Data

(63) Continuation of application No. 10/219,596, filed on Aug. 14, 2002, now Pat. No. 6,826,961, which is a continuation of application No. 09/454,128, filed on Dec. 3, 1999, now Pat. No. 6,499,348.

(51) Int. Cl.
*A61B 8/14* (2006.01)
*G01B 17/00* (2006.01)

(52) U.S. Cl. ........................... 600/459; 73/632; 73/626; 73/628; 367/153

(58) Field of Classification Search ................. 600/459, 600/437; 73/632, 627, 649, 628, 634, 862.046; 310/311; 367/153
See application file for complete search history.

(56) References Cited

U.S. PATENT DOCUMENTS 3,612,778 A 10/1971 Murphy
3,683,402 A 8/1972 Parnell
3,979,711 A 9/1976 Maginness et al.
4,064,549 A 12/1977 Cretzler
4,277,814 A 7/1981 Giachino et al.
4,295,376 A 10/1981 Bell
4,398,426 A 8/1983 Park et al.
4,420,790 A 12/1983 Golke et al.
4,490,773 A 12/1984 Moffatt
4,517,622 A 5/1985 Male
4,550,606 A * 11/1985 Drost .......................... 73/626
4,558,184 A 12/1985 Busch-Vishniac et al.
4,617,606 A 10/1986 Shak et al.
4,636,714 A 1/1987 Allen
4,866,988 A 9/1989 Brown
4,896,100 A 1/1990 Buck
4,906,586 A 3/1990 Blackburn
4,987,782 A 1/1991 Shkedi et al.
5,028,876 A 7/1991 Cadwell (Continued)

*Primary Examiner*—Eric F Winakur
*Assistant Examiner*—Katherine L Fernandez
(74) *Attorney, Agent, or Firm*—Darby & Darby P.C.; Patrick R. Turner

(57) ABSTRACT

A dynamically configurable ultrasound transducer element and related circuits and methods. The transducer may comprise an array of capacitive transducer elements, a row decoder coupled to said array of capacitive transducer elements, a column decoder coupled to said array of capacitive transducer elements, a bias voltage source coupled to said row decoder, and a driving signal source coupled to said column decoder. Preferably, a master clock also is provided to allow for a synchronization of signals between the row decoder and column decoder.

20 Claims, 4 Drawing Sheets

U.S. PATENT DOCUMENTS 5,051,937 A 9/1991 Kawate et al.
5,161,128 A 11/1992 Kenney
5,349,865 A 9/1994 Kavli et al.
5,377,524 A 1/1995 Wise et al.
5,638,822 A * 6/1997 Seyed-Bolorforosh et al. .......................... 600/459
5,671,746 A * 9/1997 Dreschel et al. ............. 600/472
5,677,965 A 10/1997 Moret et al.
5,708,368 A 1/1998 Mallory
5,750,904 A 5/1998 Doemens et al.
5,787,049 A * 7/1998 Bates ............................ 367/7
5,804,736 A 9/1998 Klauder et al.
6,014,473 A * 1/2000 Hossack et al. ............. 382/294
6,028,615 A 2/2000 Pletcher et al.
6,151,967 A 11/2000 McIntosh et al.
6,499,348 B1 * 12/2002 Mamayek .................... 73/632
6,605,043 B1 * 8/2003 Dreschel et al. ............. 600/459
6,645,145 B1 11/2003 Dreschel et al.
6,775,388 B1 * 8/2004 Pompei ...................... 381/191
6,826,961 B2 * 12/2004 Mamayek .................... 73/632

* cited by examiner

DYNAMICALLY CONFIGURABLE ULTRASOUND TRANSDUCER WITH INTEGRAL BIAS REGULATION AND COMMAND AND CONTROL CIRCUITRY

CROSS REFERENCE TO RELATED APPLICATIONS

This application is a continuation of U.S. patent application Ser. No. 10/219,596, filed Aug. 14, 2002 now U.S. Pat. No. 6,826,961, which is a continuation of U.S. patent application Ser. No. 09/454,128, filed Dec. 3, 1999, now U.S. Pat. No. 6,499,348, the entirety of which disclosures are incorporated herein by reference for all purposes.

FIELD OF THE INVENTION

The present invention relates generally to transducers for ultrasound imaging systems and, more particularly, to dynamically configurable transducers for such systems.

BACKGROUND OF THE INVENTION

Recently, substantial attention has been directed toward the development and implementation of internal and external ultrasound imaging systems.

Intraluminal, intracavity, intravascular, and intracardiac treatment and diagnosis of medical conditions utilizing minimally invasive procedures is an effective tool in many areas of medical practice. These procedures typically are performed using imaging and treatment catheters that are inserted percutaneously into the body and into an accessible vessel, such as the femoral artery, of the vascular system at a site remote from a region of the body to be diagnosed and/or treated. The catheter then is advanced through the vessels of the vascular system to the region of the body to be diagnosed and/or treated, such as a vessel or an organ. The catheter may be equipped with an imaging device, typically an ultrasound imaging device, which is used to locate and diagnose a diseased portion of the body, such as a stenosed region of an artery.

Intravascular imaging systems having ultrasound imaging capabilities generally are known. For example, U.S. Pat. No. 4,951,677, issued to Crowley, the disclosure of which is incorporated herein by reference, describes such an intravascular ultrasound imaging system. An ultrasound imaging system typically contains some type of control system, a drive shaft, and a transducer assembly including an ultrasound transducer. The transducer assembly includes a transducer element and is coupled to the control system by the drive shaft. The drive shaft typically includes an electrical cable, such as coaxial cable, for providing electrical communication between the control system and the ultrasound transducer.

In operation, the drive shaft and the transducer assembly are inserted, usually within a catheter, into a patient's body and may be positioned near a remote region of interest. To provide diagnostic scans of the remote region of interest within, for example, a coronary blood vessel, the ultrasound transducer may be positioned near or within the remote region of the patient's body. Diagnostic scans are created when the control system alternately excites and allows sensing by the ultrasound transducer. The control system may direct the ultrasound transducer toward or away from an area of the remote region. When the ultrasound transducer is excited, a transmitting/receiving surface of the transducer element creates pressure waves in the bodily fluids surrounding the ultrasound transducer. The pressure waves then propagate through the fluids within the patent's body and ultimately reach the region of interest, forming reflected pressure waves. The reflected pressure waves then return through the fluids within the patient's body to the transmitting/receiving surface of the transducer element, inducing electrical signals within the transducer element. The control system then may collect the induced electrical signals and may reposition the ultrasound transducer to an adjacent area within the remote region of the patient's body, again exciting and sensing the transducer element. This process may continue until the remote region has been examined sufficiently and a series of induced signals has been collected. The control system then may process the series of induced signals to derive a diagnostic scan and may display a complete image of the diagnostic scan.

Those skilled in the art will appreciate that the type of transducer that may be required, or preferred, for a particular procedure often will vary depending upon the type of procedure to be performed. For example, for some procedures it may be desirable to utilize a transducer with a long, or extended focus, such that areas of tissue remote from the transducer may be imaged clearly, whereas in other procedures it may be desirable to utilize a transducer with a relatively short focus to image, for example, areas of tissue in relatively close proximity to the transducer. Those skilled in the art also will appreciate that, depending upon the type of procedure to be performed, it may be desirable to utilize transducers having the ability to implement certain scanning functions. Finally, those skilled in the art will appreciate that in many imaging systems, such as those described above, a transducer will be rotated to perform a scanning function, and that the provision of such capabilities may add significantly to the cost of an imaging system.

In view of the foregoing, it is believed that a need exists for an improved ultrasound transducer that overcomes the aforementioned obstacles and deficiencies of currently available ultrasound transducers. It is further believed that a need exists for a transducer that is dynamically configurable, such that its performance may be dynamically altered to meet the needs of a given application.

BRIEF SUMMARY OF THE INVENTION

In one innovative aspect, the present invention is directed toward a dynamically configurable ultrasound transducer.

In one presently preferred embodiment, the transducer may comprise an array of capacitive transducer elements, a row decoder coupled to said array of capacitive transducer elements, a column decoder coupled to said array of capacitive transducer elements, a bias voltage source coupled to said row decoder, and a driving signal source coupled to said column decoder. Preferably, a master clock also is provided to allow for a synchronization of signals between the row decoder and column decoder.

Using the row decoder, a bias voltage may be applied to selected rows of capacitive transducer elements provided within the array to enable the function of those elements, and thereafter, a driving signal (or stimulus signal) may be supplied to selected columns of capacitive transducer elements provided within the array. In this fashion, numerous configurations of capacitive transducer elements may be activated for transmitting and receiving ultrasonic waves within a predetermined medium.

In another presently preferred embodiment, a dynamically configurable ultrasound transducer may comprise an array of capacitive transducer elements, a first pair of row and column decoders for applying a DC bias signal to selected capacitive transducer elements within the array, a second pair of row and column decoders for applying an AC driving signal to selected capacitive transducer elements within the array, and a clock for providing a master clock signal to the first and second pairs of row and column decoders.

Those skilled in the art will appreciate that different control circuits may be utilized within a dynamically configurable transducer in accordance with the present invention depending upon the performance characteristics needed from the transducer. For example, in alternative embodiments a DC bias signal by be applied to all of the capacitive transducer elements within an array, and a single row or column decoder could be utilized to selectively apply an AC driving signal to desired rows, or columns, with the array. Alternatively, a single row or column decoder circuit could be used to selectively couple both the DC bias signal and the AC driving signal to desired rows, or columns, of transducer elements within the array.

In another innovative aspect, the present invention is directed toward systems and methods for dynamically configuring an ultrasound transducer. Within such methods, a bias voltage, or a combination of a bias voltage and driving voltage, may be used to selectively activate and deactivate capacitive transducer elements provided within an array of such elements. Thus, using systems and methods in accordance with the present invention, it is possible to activate selected rows or columns of capacitive transducer elements in a predetermined sequence within a transducer element array or, alternatively, to enable and activate predetermined geometric configurations of the capacitive transducer elements within the array and in a predetermined sequence. Thus, those skilled in the art will appreciate that a dynamically configurable ultrasound transducer in accordance with the present invention may be configured in numerous ways, depending on a desired application or use of the transducer.

Other objects and features of the present invention will become apparent from consideration of the following description taken in conjunction with the accompanying drawings.

BRIEF DESCRIPTION OF THE DRAWINGS

FIG. 1(*b*) is an illustration of an alternative configuration of a capacitive transducer element and related DC bias and AC driver signal sources in accordance with a preferred form of the present invention.

DETAILED DESCRIPTION OF THE INVENTION

Figure 1A:
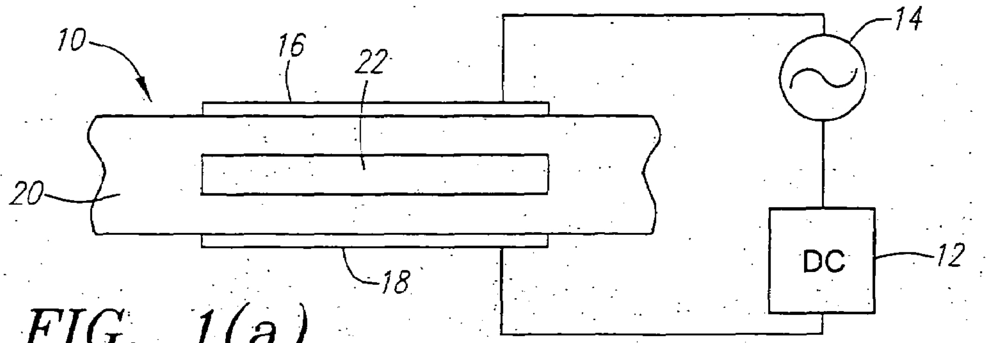
FIG. 1(*a*) is an illustration of a capacitive transducer element and related DC bias and AC driver signal sources in accordance with a preferred form of the present invention.
Figure 1B:
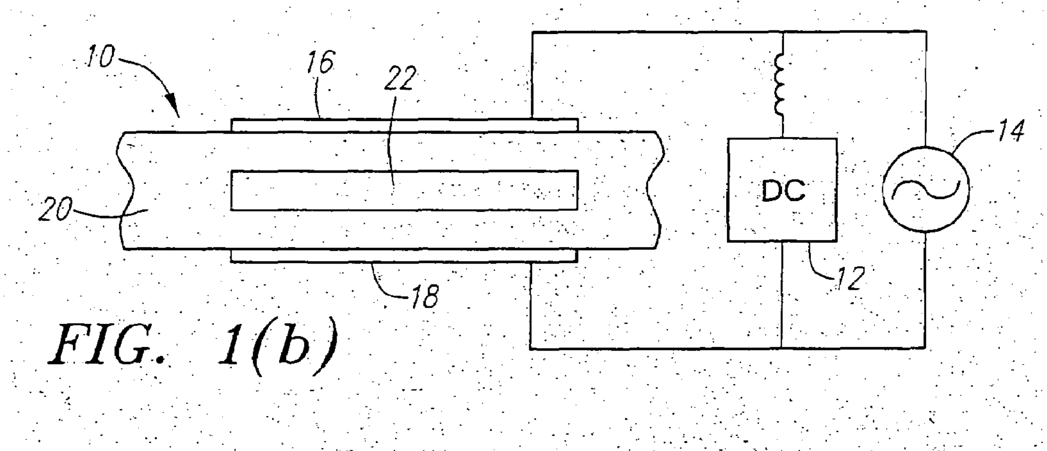

Turning now to the drawings, FIGS. 1(*a*) and 1(*b*) provide illustrations alternative embodiments of a capacitive transducer element 10, and related DC and AC signal sources 12 and 14, that may be used within a dynamically configurable ultrasound transducer 100 (shown in FIGS. 3 and 4) in accordance with the present invention. As shown, the capacitive transducer element 10 may comprise a pair of electrode plates 16 and 18 and a substrate 20. The substrate 20 is configured such that an open space 22 is provided between the electrode plates 16 and 18. A DC bias signal source 12 and an AC driving signal source 14 preferably are coupled to the electrode plates 14 and 16. The DC bias signal source 12 enables the operation of the capacitive transducer element 10, and the frequency of operation of the capacitive transducer element is determined by the AC driving signal source 14. Accordingly, those skilled in the art will appreciate that by varying the frequency of the AC driving signal source 14, it is possible to vary certain limits the frequency of operation of the capacitive transducer element. The limits of operation are imposed by the physical structure and acoustic capabilities of a given transducer element 10.

Figure 2:
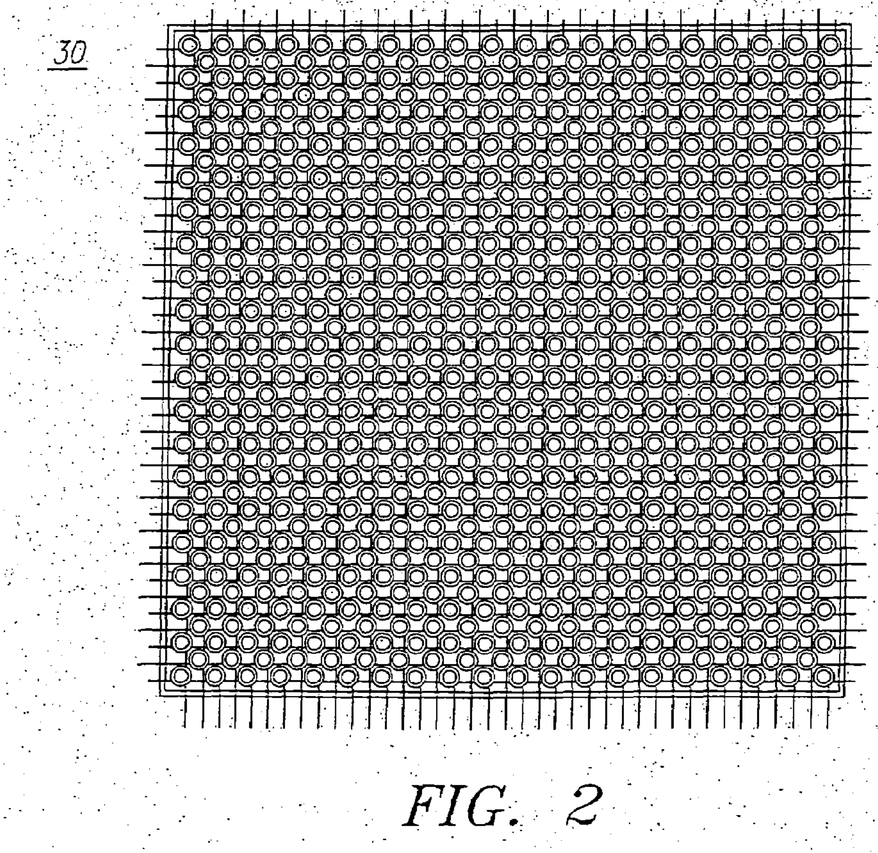
FIG. 2 is an illustration of an array of capacitive transducer elements in accordance with a preferred form of the present invention.

FIG. 2 provides an illustration of an array 30 of capacitive transducer elements 10. An array 30 of capacitive transducer elements 10 may be obtained, for example, from Sensant Corporation of San Jose, Calif.

Figure 3:
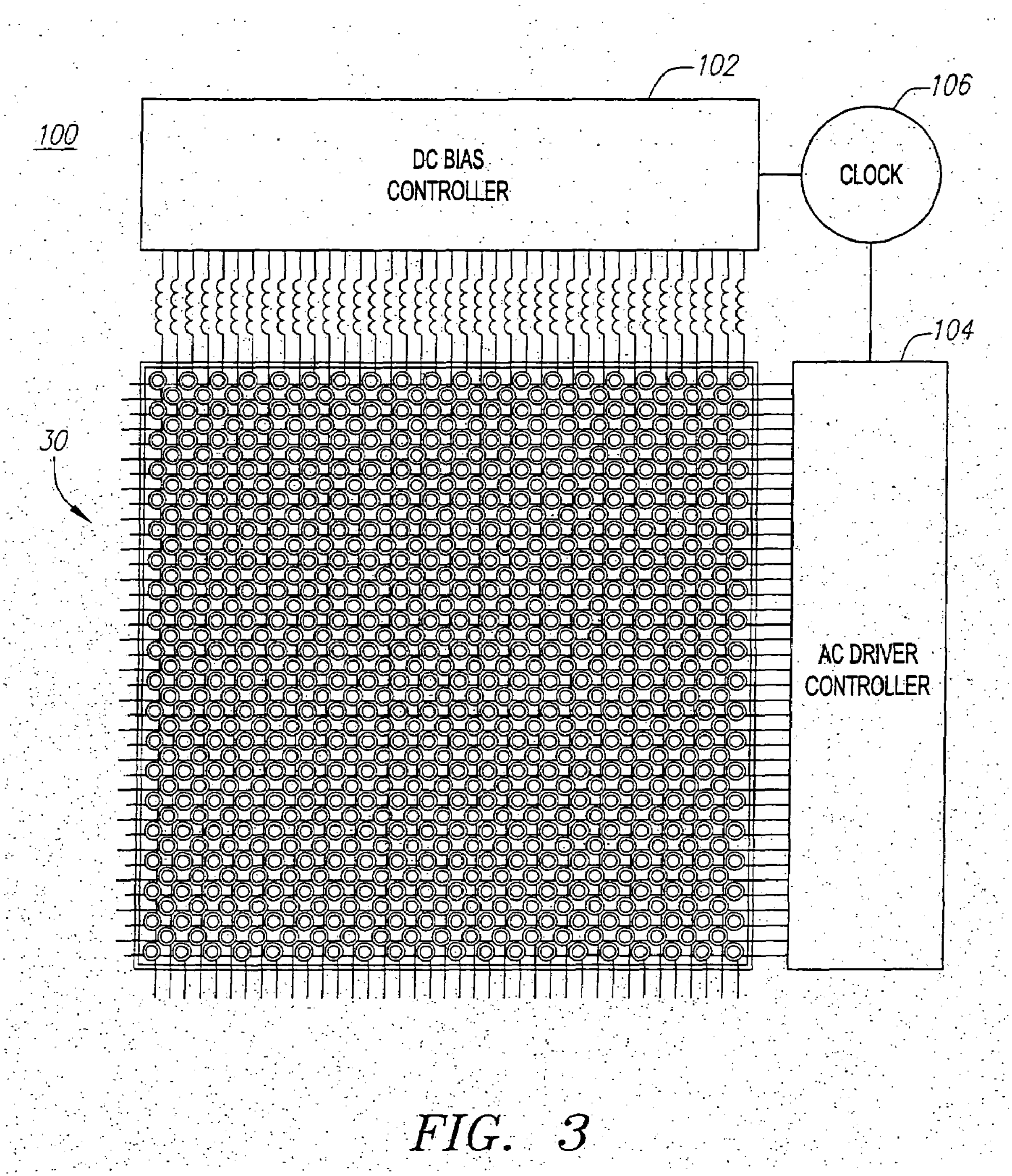
FIG. 3 is an illustration of a dynamically configurable ultrasound transducer including command and control circuitry in accordance with the present invention.
Figure 4:
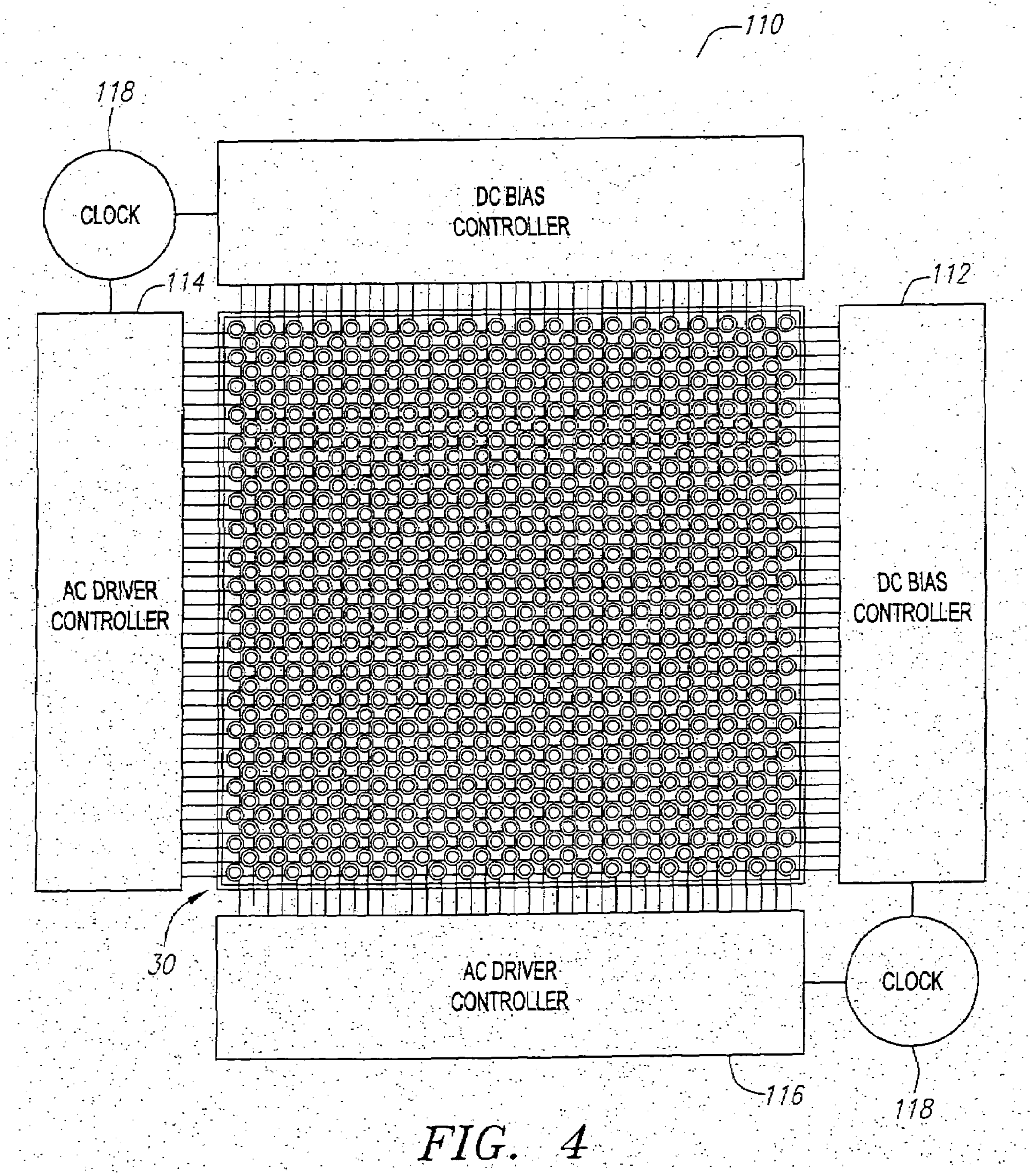
FIG. 4 is an illustration of an alternative embodiment of a dynamically configurable ultrasound transducer including command and control circuitry in accordance with the present invention.

Turning now to FIGS. 3 and 4, in one presently preferred form (shown in FIG. 3) a dynamically configurable ultrasound transducer 100 may comprise an array 30 of capacitive transducer elements 10, a DC bias controller 102, an AC driver controller 104, and a master clock 106. The DC bias controller 102 is connected to a DC bias signal source 12 (shown, for example, in FIGS. 1(*a*) and 1(*b*), and the AC driver signal controller 104 is connected an AC driver signal source 14 (also shown in FIGS. 1(*a*) and 1(*b*)). Those skilled in the art will appreciate that the DC bias controller 102 may be utilized to enable the operation of various rows or columns of capacitive transducer elements 10 within the array 30, and that the AC driver controller may be utilized to deliver an AC driver signal having a predetermined, or variable, frequency to selected rows or columns of capacitive transducer elements 10 within the array 30.

Turning now to FIG. 4, in another presently preferred embodiment, a dynamically configurable ultrasound transducer 100 in accordance with the present invention may comprise an array 30 of capacitive transducer elements 10, first and second DC bias controllers 110 and 112, first and second AC driver signal controllers 114 and 116, and a master clocking circuit 118 coupled to the various controllers 110-116. Preferably, array 30 of capacitive transducer elements 10, the first and second DC bias controllers 110 and 112, the first and second AC driver signal controllers 114 and 116, and the master clocking circuit 118 are formed on or within a single substrate or comprise a single overall unit. The construction, operation, and implementation of clocking circuits, row decoders, and column decoders are believed to be well known in the art. Thus, the specific structures of the DC bias controllers 102, 110, and 112, AC driving signal controllers 104, 114, and 116, and clock circuits 106 and 118 are not described herein in detail.

Figure 5A:
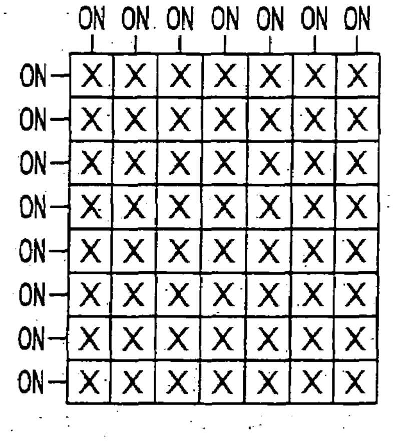
FIGS. 5(*a*)-5(*c*) illustrate how capacitive transducer elements within an array in accordance with the present invention may be selectively activated to achieve desired transducer configurations.
Figure 5B:
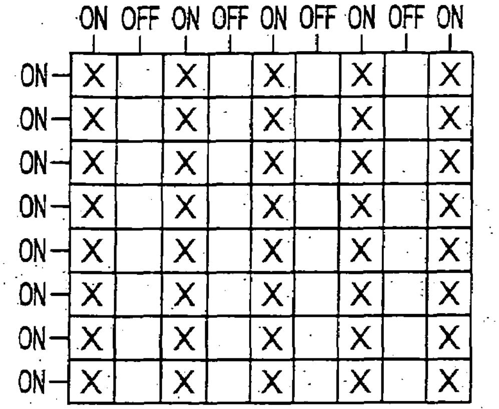
Figure 5C:
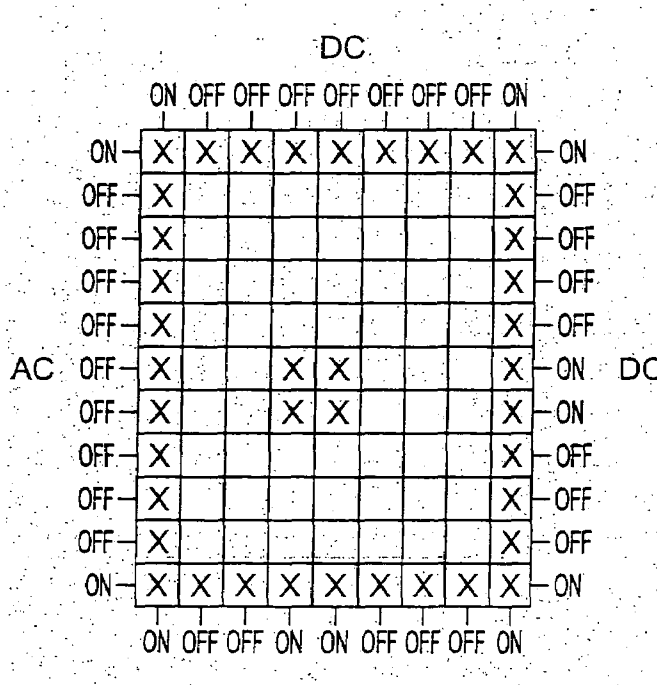

Turning now also to FIGS. 5(*a*)-5(*c*), those skilled in the art will appreciate that by utilizing a dynamically configurable ultrasound transducer 100 in accordance with the present invention, it is possible to achieve numerous transducer configurations and, if desired, to vary those configurations in real time. For example, as shown in FIG. 5(*a*) for some applications it may be desirable to enable the function of all of the capacitive transducer elements 10 within a given array 30 and to use the entire array 30 as an annular device. Alternatively, as shown in FIG. 5(*b*) it may be desirable for certain ultrasound scanning procedures to enable rows or columns of transducer elements 10 in a synchronized fashion. Finally, in still other applications, it may be desirable to enable predetermined geometric configurations of the transducer elements 10 in a synchronized fashion. Moreover, by selectively enabling predetermined geometric patters of transducer elements 10 in a synchronized fashion, variations in transmission and reception aperture sizes may be achieved, variations in the focal length of the transducer 100 may be achieved, the transducer 100 may be used as a phased array, and the transducer 100 may effect electronic scanning.

Those skilled in the art also will appreciate that by properly controlling the DC bias and AC driving signal controllers within a transducer 100 in accordance with the present invention, it is possible to operate the transducer 100 as an annular array device, a one dimensional (1D) array, a two dimensional (2D) array, or a three dimensional (3D) array.

Figure 6:
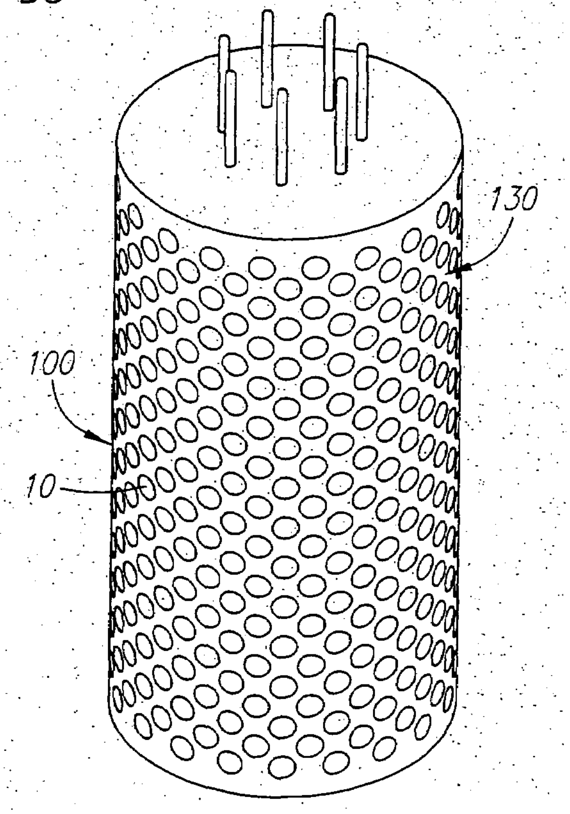
FIG. 6 is an illustration of a cylindrical ultrasound transducer in accordance with one form of the present invention.

Turning now to FIG. 6, in a presently preferred embodiment, and ultrasound transducer 100 may take the form of a imaging cylinder, such that a plurality of capacitive transducer elements 10 are provided around the exterior surface 130 of the cylindrical structure, and the command and control circuits (not shown) may be provided within the core (not shown) of the cylindrical structure. Those skilled in the art will appreciate that an ultrasound transducer 100 configured in the manner illustrated in FIG. 6 might be used to effect radial ultrasonic imaging scans within, for example, the coronary artery of a patent without the use of transducer rotation hardware and related image artifact.

While the present invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

What is claimed is:

1. A dynamically configurable ultrasound transducer comprising:

a three-dimensional array of capacitive transducer elements, a first decoder coupled to said array of capacitive transducer elements, a second decoder coupled to said array of capacitive transducer elements, a DC bias voltage source coupled to said first decoder, and an AC driving signal source coupled to said second decoder, wherein the DC bias voltage source is coupled to said first decoder without coupling to said second decoder, and wherein the AC driving signal is coupled to said second decoder without coupling to said first decoder.

2. The dynamically configurable ultrasound transducer of claim 1 further comprising a master clock coupled to said first decoder and said second decoder.

3. The dynamically configurable ultrasound transducer of claim 1, wherein said first decoder and second decoder comprise a row decoder and column decoder, respectively.

4. The dynamically configurable ultrasound transducer of claim 1, wherein said first decoder and second decoder comprise a column decoder and row decoder, respectively.

5. The dynamically configurable ultrasound transducer of claim 1, further comprising an imaging cylinder having an exterior surface, wherein the three- dimensional array of capacitive transducer elements are coupled to the exterior surface of the imaging cylinder.

6. The dynamically configurable ultrasound transducer of claim 5, wherein at least one of the first decoder or the second decoder is disposed within the imaging cylinder.

7. The dynamically configurable ultrasound transducer of claim 1, wherein the three-dimensional array of capacitive transducer elements are configured to operate in predetermined geometric patterns.

8. The dynamically configurable ultrasound transducer of claim 1, wherein transmission and reception apertures of the three-dimensional array of capacitive transducer elements are configurable.

9. The dynamically configurable ultrasound transducer of claim 1, wherein a focal length of the three-dimensional array of capacitive transducer elements is configurable.

10. The dynamically configurable ultrasound transducer of claim 1, wherein the three-dimensional array of capacitive transducer elements is substantially entirely cylindrical in shape.

11. A dynamically configurable ultrasound transducer comprising:

an array of capacitive transducer elements;

a DC bias voltage source coupled to the capacitive transducer elements, an AC driving signal source coupled to the capacitive transducer elements, a DC bias decoder coupled to the capacitive transducer elements and the DC bias voltage source, wherein the DC bias decoder is configured and arranged to selectively apply only a DC bias voltage, and wherein the DC bias voltage is from the DC bias voltage source; and an AC decoder coupled to the capacitive transducer elements and the AC driving signal source, wherein the AC decoder is configured and arranged to selectively apply only an AC driving signal, wherein the AC driving signal is from the AC driving signal source, and wherein the selective application of the DC bias voltage by the DC bias decoder and selective application of the AC driving signal by the AC decoder generates a pattern of active transducer elements from the array of capacitive transducer elements.

12. The transducer of claim 11, wherein the DC bias decoder comprises at least one of a row decoder or a column decoder, wherein the AC decoder comprises a column decoder when the DC bias decoder comprises a row decoder, and wherein the AC decoder comprises a row decoder when the DC bias decoder comprises a column decoder.

13. The transducer of claim 11, wherein the array of capacitive transducer elements is substantially entirely cylindrical in shape.

14. The transducer of claim 11, further comprising an imaging cylinder having an exterior surface, wherein the three dimensional array of capacitive transducer elements are coupled to the exterior surface of the imaging cylinder.

15. The transducer of claim 14, wherein at least one of the DC bias decoder or the AC decoder is disposed within the imaging cylinder.

16. The transducer of claim 11, wherein the AC decoder is configured and arranged to transmit AC driving signals at a plurality of frequencies.

17. The transducer of claim 11, wherein the AC decoder is configured and arranged to selectively apply the AC driving signal to the capacitive transducer elements at a plurality of frequencies.

18. The transducer of claim 11, further comprising a master clock coupled to the DC bias decoder and the AC decoder.

19. The transducer of claim 11, further comprising a second DC bias decoder coupled to the capacitive transducer elements and the DC bias voltage source.

20. The transducer of claim 11, further comprising a second AC decoder coupled to the capacitive transducer elements and the AC driving signal source.

* * * * *